United States Patent
Robinson

(10) Patent No.: US 8,450,244 B2
(45) Date of Patent: May 28, 2013

(54) MIXTURES OF MUSTARD PLANT MATERIAL FOR THE CONTROL OF PESTS AND METHODS OF MAKING

(75) Inventor: James Robinson, Hague (CA)

(73) Assignee: MPT Mustard Products & Technologies Inc., Saskatoon, Saskatchewan (CA)

( * ) Notice: Subject to any disclaimer, the term of this patent is extended or adjusted under 35 U.S.C. 154(b) by 0 days.

(21) Appl. No.: 13/273,642

(22) Filed: Oct. 14, 2011

(65) Prior Publication Data
US 2012/0122685 A1 May 17, 2012

Related U.S. Application Data

(60) Provisional application No. 61/424,771, filed on Dec. 20, 2010.

(51) Int. Cl.
*A01N 63/00* (2006.01)

(52) U.S. Cl.
USPC .......................................................... 504/118

(58) Field of Classification Search
None
See application file for complete search history.

(56) References Cited

U.S. PATENT DOCUMENTS

| | | | |
|---|---|---|---|
| 5,717,056 A | 2/1998 | Varadarajan et al. | |
| 6,545,043 B1 | 4/2003 | Coats et al. | |
| 6,599,514 B1 * | 7/2003 | Greenland et al. | 424/404 |
| 7,087,553 B2 | 8/2006 | Riordan | |
| 2003/0194455 A1 * | 10/2003 | Taylor | 424/755 |
| 2005/0065034 A1 * | 3/2005 | Miele et al. | 504/367 |
| 2008/0182751 A1 * | 7/2008 | Morra et al. | 504/117 |

OTHER PUBLICATIONS

Handiseni, M., "Fungicidal and herbicidal properties of *Brassica nupus*, *Brassica juncea* and *Sinapis alba* seed meal amended soils and phytotoxicity on tomato and pepper." A Thesis, University of Idaho, Jan. 2009, pp. 1-141.*

Morra, M. J, 2000-2002, Subcontract Report National Renewable Energy Laboratory NREL/SR-510-36208.

Brown, J. and Morra, M. J, 2005, Subcontract Report National Renewable Energy Laboratory NREL/SR-510-35254).

* cited by examiner

*Primary Examiner* — James H Alstrum Acevedo
*Assistant Examiner* — Monica Shin
(74) *Attorney, Agent, or Firm* — Bereskin & Parr LLP/S.E.N.C.R.L., s.r.l.; Micheline Gravelle

(57) ABSTRACT

A composition for controlling pests comprising a mixture of plant material obtainable from a mustard plant of the species *Sinapis alba* and plant material obtainable from a mustard plant of the species *Brassica juncea* is described.

12 Claims, 6 Drawing Sheets

MIXTURES OF MUSTARD PLANT MATERIAL FOR THE CONTROL OF PESTS AND METHODS OF MAKING

RELATED APPLICATION

This application claims the benefit under 35 USC §119(e) of U.S. Provisional application No. 61/424,771 filed Dec. 20, 2010 which is incorporated herein by reference in its entirety.

FIELD OF THE DISCLOSURE

The disclosure provided herein relates to novel mustard plant material comprising compositions and methodologies for making them. These compositions are useful for the treatment of pests.

BACKGROUND OF THE DISCLOSURE

Pesticides are used to control pests in areas such as crops, homes, and food storage areas. However the large scale use of pesticides, particularly in the second half of the twentieth century and early twenty first century, has resulted in significant concerns with respect to the environmental impact, increased resistance against pesticides in the pest populations, as well as toxicity to non-target organisms, including humans. Controversial is for example the use of polychlorinated hydrocarbons, such as DDT, as they persist for extended periods of time in the environment and are harmful for example to fish and birds of prey. Another class of pesticides, methylbromides, in addition to being toxic to the human nervous and respiratory system, poses damage to the stratospheric ozone layer, as a result of which governments in many jurisdictions have been severely restricting the use of methylbromides. Other widely used efficacious pesticides include organophosphates and carbamates, and while these compounds decompose more rapidly in the environment, they are still considered highly toxic.

One alternative is the use of pesticides obtainable from natural sources, also referred to in the art as biopesticides. These biopesticides are prepared from sources such as plants which frequently comprise natural defenses against insects and other pests. Glucosinolates which are ubiquitously found within the mustard plant family (also alternatively known to the art as "Cruciferae" or Brassicaceae"), which includes for example, mustard and rapeseed, act as pesticides in many plants. The pesticidal efficacy of mustard plant material is attributable to glucosinolate breakdown products, including allyl thiocyanate and allyl isothiocyanate, rather than glucosinolates themselves. These glucosinolate degradation products are formed following an enzymatic reaction involving enzymes endogenously present in mustard plant material.

Pesticide products based on mustard plant material are known to the prior art. US Patent Application 2008/0182751, for example, discloses the use of mustard plant material to control plant pests, including insects, and U.S. Pat. No. 5,717,056 teaches the use of mustard bran to control soil pests. The use of mustard meal to control plant pests is disclosed in Brown, J. and Morra, M. J, 2005, Subcontract Report National Renewable Energy Laboratory NREL/SR-510-35254. Purified products and organic extracts obtainable form mustard plants for use of the treatment of pests are also known to the prior art. In this regard U.S. Pat. No. 7,087,553 discloses a process for eliminating unwanted organisms in agriculture comprising the co-application of mustard oil in water and a solution of phosphorus in water. U.S. Pat. No. 6,545,043 teaches methods for suppressing target pests using a composition comprising a purified glucosinolate breakdown product obtainable from mustard plants. Mustard meal based glucosinolate products have been demonstrated to exhibit inhibitory effects against arthropods, as well as weeds, fungi and bacteria (see: Brown, J. and Morra, M. J, 2005, Subcontract Report National Renewable Energy Laboratory NREL/SR-510-35254).

Notwithstanding the foregoing, the potency of the mustard plant material derived pesticides known to the prior art is lower than desirable, allowing for limited pest control, and requiring the use and application of substantial volumes of mustard plant material in order to control the pests.

There therefore still are significant shortcomings in mustard plant material based formulations capable of controlling pests that are known to the prior art. In particular, there is a need for a more potent pesticide prepared from mustard plant material, allowing for the application of less mustard plant material and less expensive pesticide formulations.

SUMMARY OF THE DISCLOSURE

The present disclosure provides novel formulations comprising mustard plant material that are useful in the treatment of pests. The formulations herein disclosed are superior to the heretofore known mustard plant material based formulations in many respects, including with respect to their potency, ease of manufacture and ease of application.

Accordingly, the present s provides a composition for controlling pests comprising a mixture of (a) a plant material obtainable from a mustard plant of the species *Sinapis alba*, and (b) a plant material obtainable from a mustard plant of the species *Brassica juncea*, said composition comprising an effective amount of a glucosinolate breakdown product.

In preferred embodiments of the present disclosure the plant material obtained or obtainable from either *Sinapis alba* or *Brassica juncea* is a mustard seed meal. In a further preferred embodiment the plant material obtained or obtainable from both *Sinapis alba* and *Brassica juncea* is a seed meal.

The present disclosure further provides methods for preparing a pesticide composition comprising mixing a plant a material obtainable from a mustard plant of the species *Sinapis alba*, with a plant material obtainable from a mustard plant of the species *Brassica juncea*, said mixture comprising an effective amount of a glucosinolate breakdown product and formulating said mixture into a pesticide composition.

The present disclosure also provides a method for controlling pests comprising applying to a pest a composition comprising (a) a plant material obtainable from a mustard plant of the species *Sinapis alba*, and (b) a plant material obtainable from a mustard plant of the species *Brassica juncea*, said composition comprising an effective amount of a glucosinolate breakdown product.

The present disclosure still further provides a method for controlling pests comprising
 (a) preparing a composition comprising a mixture of:
  (i) a plant material obtainable from a mustard plant of the species *Sinapis alba*; and
  (ii) a plant material obtained from mustard plant of the species *Brassica juncea;*
 said mixture comprising an effective amount of a glucosinolate breakdown product; and
 (b) applying the composition to a pest.

Other features and advantages of the present disclosure will become apparent form the following detailed description. It should be understood, however, that the detailed description and the specific examples, while indicating preferred embodiments of the disclosure, are given by way of

DETAILED DESCRIPTION OF THE DISCLOSURE

Figure 1:
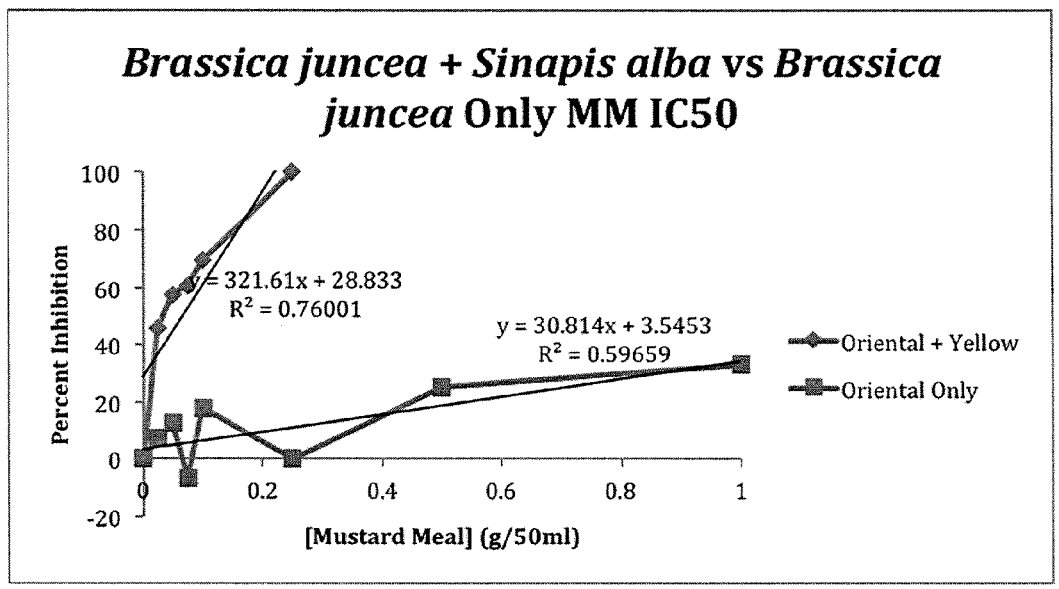
FIG. 1 depicts the inhibition of *R. solani* mycelial growth using various concentrations of a mixture of *Brassica juncea* and *Sinapis alba* mustard meal versus *Brassica juncea* meal alone.

As hereinbefore mentioned, the present disclosure relates to novel compositions comprising mustard plant material for use in the control of pests. The present inventor has surprisingly found that a mixture of plant material obtained from a mustard plant of the species *Sinapis alba*, and a plant material obtainable from a mustard plant of the species *Brassica juncea*, may be used to prepare a formulation exhibiting superior pesticide characteristics. In particular, the compositions provided herein, surprisingly, permit control over the enzymatic reaction responsible for the conversion of glucosinolates into pesticidally active products, thus allowing for the preparation of compositions with a wide range of varying potencies. In addition, the potencies that may be achieved using the compositions of the present disclosure exceed the potencies of mustard meal based compositions known to the prior art. Furthermore the formulations herein provided may be prepared in a manner that permits the preparation of compositions with a variety of granular sizes, thus allowing for the preparation of pesticide formulations other than powder based formulations. The compositions prepared in accordance with the present disclosure also break down more readily than conventional mustard plant material based formulations, resulting in a reduction or elimination of the amount of residue left on the surface to which the pesticide product is applied. Finally, the compositions provided herein are additionally beneficial in that they are natural, organic and biodegradable.

Accordingly, the present disclosure provides a composition for controlling pests comprising a mixture of (a) a plant material obtained or obtainable from a mustard plant of the species *Sinapis alba*, and (b) a plant material obtained or obtainable from a mustard plant of the species *Brassica juncea*, said composition comprising an effective amount of a glucosinolate breakdown product.

The terms "*Sinapis alba*" (also interchangeably referred to herein as "yellow mustard") and "*Brassica juncea*" (also interchangeably referred to herein as "Oriental mustard") as used herein refer to any plants of these mustard plants species, including any cultivars thereof.

The term "glucosinolate breakdown product" refers to products obtainable following hydrolysis of glucosinolate. The general structure of glucosinolate is:

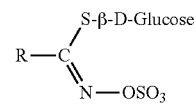

Examples of glucosinates that may be found in the plant material used in accordance with the present disclosure are epiprogoitrin, sinigrin and sinalbin. Included within the term "glucosinolate breakdown products", are the following three general classes of glucosinolate breakdown products:

Further glucosinolate breakdown products include 1-cyano-2-hydroxy-3-butene ("CHB") and goitrin, which are obtained following the breakdown of the glucosinolate epiprogoitrin. Further glucosinolate breakdown products include allyl thiocyanate ("ATC"), allyl isothiocyanate ("AITC") and allyl cyanide ("AC") all of which are breakdown products of the glucosinolate sinigrin. Still further glucosinolate breakdown products include hydroxyl benzols.

Mustard Plant Material

In accordance with the present disclosure any plant material obtained or obtainable from *Brassica Juncea* and *Sinapis alba* mustard plants may be used, including any mustard plant material, or processed plant material, obtained or obtainable from the leaves, stems, roots or seeds of these mustard plants. Preferably the plant material as used herein is treated such as to produce a processed plant material. The plant material may for example be crushed or pressed to obtain a crushed or pressed mustard plant material. Preferably the *Brassica juncea* and *Sinapis alba* mustard plant material or processed mustard plant material used in accordance herewith is moistened using water and homogenized in order to promote the hydrolysis of glucosinolates. Pre-treatment of the plant material is preferred for certain plant materials, such as seed. Pre-treatment processes that may be used in accordance herewith include dehulling, cracking, grinding, flaking, pressing, extruding, pelleting and the like. When oil rich mustard plant material is used in accordance herewith, it is preferable to remove the oil from the mustard plant material. This may be accomplished through methods such as solvent extraction, hydraulic pressing, expeller pressing, cold pressing and other oil removal processes that will be well known to the skilled artisan. Since the hydrolysis of glucosinolates is performed by the heat labile enzyme plant enzyme myrosinase it is preferred that all pre-treatment steps are performed at temperatures below 60° C., more preferably below 50° C. and most preferably below 35° C.

In a preferred embodiment of the present disclosure, the processed *Brassica Juncea* and *Sinapis alba* plant material used is a mustard seed meal. Many processes for processing raw mustard seed into oil and meal known to the art. Illustrative processes are those taught by and Morra, M. J, 2000-2002, Subcontract Report National Renewable Energy Laboratory NREL/SR-510-3628. Typical of these processes is the receipt of mustard seed from the field by conventional transport means, for example, rail or truck, in a dirty and often wet condition. The mustard seed is then subjected to an elementary separation procedure, for example, contacted with a vibrating screen or using a grain cleaning machine, for example a grain cleaning machines manufactured by Damas A/S (Denmark), in which the mustard seed is separated from non-mustard seed material, such as rocks, sticks, dirt, leaves, weed seeds, loose hulls etc. It is preferred that following the cleaning the mustard seed is dried, using for example a grain dryer as manufactured by Vertec Industries Limited (Canada), so that the moisture content of the seed is reduced to between 5% and 7%. Following the removal of non-mustard seed contaminants and drying the mustard seed may be stored, mixed with other mustard seed, or processed to obtain mustard seed meal. At this point in the process the outer seed coating, which is also known as the seed husk or bran, may be removed from the seed by milling or cracking the seed or using another suitable abrasive process to obtain the seed kernel. Such removal of the bran is however optional and not of critical importance. The next step in the process is largely dependent on the oil (also known as "lipid" or "fat") content of the mustard meal that is desired. If a "full fat" meal is desired than the kernels are subjected to a process that does not result in oil extraction. If, on the other hand a "defatted" meal is desired than the kernels are subjected to a process resulting in oil extraction. In preferred embodiments of the present disclosure a defatted meal is prepared. Accordingly the mustard seed or mustard kernel (in instances where the bran has been removed) is preferably ground, using for example a hammer mill, to obtain mustard flour. Thereafter the oil is removed from the flour by for example chemical extraction, using for example hexane, or mechanical extraction using for example an oil expeller or press, such as an oil press such as a Täby Press manufactured by Skeppsta Maskin AB (Sweden) or a Komet oil expeller manufactured by Monforts Oekotec GmbH (Germany). Preferably the mustard seed meal used in accordance with the present disclosure comprises between 2% and 50% of the available seed oil, and more preferably approximately between 10 and 15%, and most preferably 15% of the available seed oil. In preferred embodiments of the present disclosure, the mustard seed meal obtained at this point in the process is ready for use as an ingredient for formulation with other optional ingredients referred to in this application.

It is noted that at various stages in the process the mustard plant materials of the species *Sinapis alba* and *Brassica juncea* may be mixed. For example the hereinbefore described process for seed meal preparation may be used to prepare separate seed meal fractions from *Sinapis alba* and *Brassica juncea*. Upon having obtained such meal fractions, the meal fractions may be mixed and a blended meal may be obtained. In an alternative embodiment of the present disclosure seeds of *Brassica juncea* and *Sinapis alba* may be mixed, and the seed meal may be prepared from the seed mixture. In a further preferred embodiment of the present disclosure, a meal fraction of *Brassica juncea* is prepared and alternate mustard plant material form *Sinapis alba*, for example a bran fraction, is added.

The mixing ratio of the *Brassica juncea* and *Sinapis alba* plant material or processed plant material may vary and by varying the mixing ratio of *Brassica juncea* and *Sinapis alba* plant material, the potency of the final pesticide formulation may be controlled. Preferably, when using mustard meal, from about 0.3 percent to about 15 percent (w/w) of *Sinapis alba* mustard meal is mixed with from about 99.7 percent to about 85 percent (w/w) of *Brassica juncea* meal. In preferred embodiments, 1 percent to 2 percent (w/w); 2 percent to 3 percent (w/w); 3 percent to 4 percent (w/w); 5 percent to 6 percent (w/w); 6 percent to 7 percent (w/w); 7 percent to 8 percent (w/w); 8 percent to 9 percent (w/w); 9 percent to 10 percent (w/w); 10 percent to 11 percent (w/w); 11 percent to 12 percent (w/w), 12 percent to 13 percent (w/w); 13 percent to 14 percent (w/w); or 14 percent to 15 percent (w/w) *Sinapis alba* meal is used, and the balance made up by *Brassica juncea* meal. In a particularly preferred embodiment, 2 percent (w/w) of *Sinapis alba* mustard meal is mixed with 98 percent (w/w) of *Brassica juncea* meal. The AITC concentrations in the blended mustard meal product preferably range between 1 percent and 5 percent (w/w) of the combined mustard seed meal. Such concentrations may be attained by mixing from about 98 percent (w/w) of *Brassica juncea* meal with 2 percent (w/w) of *Sinapis alba* mustard meal.

Preparation of Pesticide Formulations

The pesticide formulations prepared in accordance with the present disclosure preferably comprises a carrier. Carriers that may be used in accordance with the present disclosure include any compound capable of carrying and/or delivering the pesticides to the target pest, including any oils, including any type of vegetable oil, such as Canola oil, soybean oil and the like, polymers, plastics, wood, gels, colloids, sprays, drenching means, emulsifiable concentrates and so forth. The selection of the carrier and the amount of carrier used in a formulation may vary and depends on several factors including the specific pesticide use and the preferred mode of application.

In accordance with the present disclosure in preferred embodiments of the present disclosure a sugar is included in the formulation. In accordance with the present disclosure, any sugar may be used, including any monosaccharide, disaccharide, trisaccharide, oligosaccharide or polysaccharide. Monosaccharides that may be used in accordance with the present disclosure include any tretrose, pentose, hexose or heptose. Tetroses that may be used include erythose and threose. Pentoses that may be used include arabinose, ribose, ribulose, xylose, xylulose and lyxose. Hexoses that may be used in accordance with the present disclosure include allose, altrose, fructose, galactose, glucose, glulose, idose, mannose, sorbose, talose, and tagatose. Heptoses that may be use include seduheptulose. Disaccharides that may be used in accordance with the present disclosure include sucrose, maltose, trehalose, lactose and melibiose. Trisaccharides that may be used include raffinose. Polysaccharides that may be used e.g. glycogen, starch, dextran. Any of the foregoing sugars may be used in more or less pure form. In addition mixtures of sugars may be used in accordance with the present disclosure. In preferred embodiments of the present disclosure the sugar that is used is sucrose.

In preferred embodiments of the present disclosure, the pesticide the sugars are mixed with the blended mustard meal in concentrations varying from 0.5% and 8% w/w. The sugar and mustard plant material are preferably thoroughly mixed in such a manner that a homogenous mixture is obtained using for example a ribbon blender (e.g. a ribbon blender manufactured by Munson Machinery Co (USA)). It is further preferred that the mustard plant material and the sugar are mixed in the presence of water. The amount of water that is used may vary but preferably ranges from 8% w/v to 4% w/v. Mixing of the mustard plant material or processed mustard plant material and sugar may conveniently be performed at ambient temperatures. The seed meal-sugar mixture thereafter is preferably further treated using milling, grinding or pelletizing devices, such as a CPM pellet mill manufactured by CPM (USA), to obtain pellets with a preferred size between 2 mm and 6 mm. Thereafter the pellets may be treated by a device capable of crumbling the pellets, using for example a roll crumbler, such as manufactured by Apollo (USA) and separated for granular size using one or more screening devices comprising gauges which permit the separation of the crumbled pellets into fractions of various sizes, which may be vibrating or rotating screens. Using a rotary screen separator, for example such as manufactured by Peacock Industries (Canada), comprising multiple screens with different of gauges it is possible to obtain products with a range of different granular sizes. Thus the present disclosure permits the preparation of formulations comprising mustard plant material, including mustard meal, and a sugar wherein the granular size of the formulation can be readily controlled and be set as desired. Preferably granular size in formulations prepared in accordance with the present disclosure ranges between 0.01 mm and 10 mm. The concentrations of glucosinolates in the final formulated product may vary but typically ranges between 95 and 225 µmoles/gram. The concentration glucosinolate breakdown product present in the formulations prepared in accordance with the present disclosure also may vary. Typically AITC is present in the final formulation in concentrations of at least 10 µmoles/gram and more preferably between 10 and 200 µmoles/gram and most preferably between 10 and 90 µmoles/gram. Within the foregoing concentration ranges the glucosinolate breakdown products of the present disclosure are effective in that they provide for a reduction or limitation of the incidence or severity of the pest infestation or activity for a limited or more prolonged period of time.

Other ingredients that may be used in the formulation of the final product accordance with the present disclosures include mustard bran, and emulsifiers. The mustard bran that may be used may be from the same or from a different species of mustard as the starting mustard plant material that is used. Any additional ingredients that are used in accordance with the present disclosure, in embodiments of the present disclosure where mustard meal is used are preferably co-mixed with the sugar and mustard meal prior to pelletizing of the product. The final pesticide preparation may be formulated as a spray, liquid, dust, fume or powder or in any other form as desired.

As hereinbefore mentioned, the present disclosure further provides methods for preparing a pesticide composition comprising (a) providing a material obtainable from a mustard plant comprising an effective amount of a glucosinolate breakdown product and (b) mixing the material obtained from mustard plants with a sugar. In preferred embodiments of the present disclosure mustard seed meal is used to as the material obtained from mustard plants.

Use of the Pesticide Formulations

The compositions provided herein may be used to control pests. Accordingly the present disclosure also provides a method for controlling pests comprising applying to a pest a composition comprising (a) a plant material obtainable from a mustard plant of the species *Sinapis alba*, and (b) a plant material obtainable from a mustard plant of the species *Brassica juncea*, said composition comprising an effective amount of a glucosinolate breakdown product.

The present disclosure still further provides a method for controlling pests comprising
(a) preparing a composition comprising a mixture of:
  (i) a plant material obtainable from a mustard plant of the species *Sinapis alba*; and
  (ii) a plant material obtained from mustard plant of the species *Brassica juncea;*
  said mixture comprising an effective amount of a glucosinolate breakdown product; and
(b) applying the composition to a pest.

The target pest may be any pest, including any prokaryotic pest, including any prokaryotic pest belonging to the Monera kingdom, and any eukaryotic pest belonging to the Protista, fungal, plant and animal kingdoms. Accordingly pests to which the compositions of the present disclosure may be applied include any insect, arachnid or crustacean pest, including ticks, mites, weevils, ants, mosquitoes etc. Further pests to which the compositions of the present disclosure may be applied are worms and nematodes. As hereinbefore mentioned formulations with different granular sizes may be prepared in accordance with the present disclosure. Granular sizes of 0.01-0.25 mm are particularly suitable for application in fluid suspensions and pesticides applied through irrigation. Granular sizes ranging from 0.25 mm to 0.75 mm are particularly suitable for topical application to surface areas, for example application to turf. Granular sizes from 2 mm to 6 mm are particularly suitable for incorporation in soil and treatment of crops including for example potatoes and strawberries. The delivery route to the pests may vary and may be as desired for example the pesticide product may be delivered as a fumigant, or through aquatic exposure or direct contact. Upon application of the pesticide to the pest, the incidence or severity of the pest infestation or activity will be limited or reduced at least for a limited or more prolonged period of time, and as such the novel methods and compositions disclosed herein provide a means to control pests.

The present disclosure is further described by reference to the following examples which are illustrative only and not limiting the disclosure.

Example 1

Preparing Mustard Plant Material Obtained from *Brassica juncea* and a Mustard Plant Material Mixture Obtained from *Brassica juncea/Sinapis alba*

One metric ton of *Brassica juncea* mustard seed was dried using a Vertec grain dryer, model VT5000 set at a temperature not exceeding 55° C., yielding approximately 985 kg of dried mustard seed having a moisture content of 6.5%. The dried mustard seed was subsequently cleaned using a Damas screen Model 640 ana, yielding approximately 960 kg of seed. The cleaned seed was then subjected to a de-oiling process using a Taby Type 90 oil expeller. The de-oiling process was carried out maintaining a temperature of less than 55° C. and provided seed meal comprising 30% of the total available seed oil content, yielding approximately 672 kg of the *Brassica juncea alba* seed meal. To the de-oiled meal 16 kg of sucrose and 134 kg of *Brassica juncea* bran was added and the formulation was then mixed using a Munson ribbon blender, model 210 yielding a mixture of approximately 822 kg. The mixture was pelleted using a CPM pellet mill (CPM Master Series) at 50° C. The performance of this process did not result in any substantial yield loss. The pelleted product was thereafter subjected to crumbling using an Apollo roll crumbler, Model 10 having its fluted rolls set at 3 mm-3.5 mm. Again the foregoing process did not result in any substantial yield loss.

The crumbled material was then screened using a rotary screen unit (Peacock Industries Inc.) comprising a 10×10×24 gauge load screen and a 4×36×32 finish screen. This yielded three separate fractions: (1) 131 kg of a fraction with granular size of 0.01-0.25 mm; (2) 543 kg of a fraction with a granular size of 0.25 mm-0.75 mm; and (3) 148 kg of a fraction with a granular size of 2 mm-6 mm. A mixture of *Brassica juncea/Sinapis alba* was prepared by blending dried *Brassica juncea* seed with dried *Sinapis alba* seed 98/2% (w/w) using a standard hopper and thereafter following the methodology described above.

Example 2

Comparison of AITC Content

Separate mustard meal fractions comprising *Brassica juncea* and *Sinapis Alba* were prepared as described in Example 1. In addition, a blended meal fraction comprising 98 percent (w/w) of *Brassica juncea* and 2 percent (w/w) *Sinapis alba* was prepared by mixing *Brassica juncea* (98 percent (w/w)) and *Sinapis alba* seed (2 percent (w/w)) again following the formulation methodology as described in Example 1. The AITC content was measured and the following results were obtained:

|  | Sinapis Alba | Brassica juncea | Sinapis Alba/Brassica juncea blend |
|---|---|---|---|
| AITC Yield | 0.5-1.0% | 0.5-1.0% | 3.0% |

Example 3

Pesticide Efficacy of *Brassica juncea* and *Sinapis alba* Mustard Mixture Against *Rhizoctonia solani*

A mustard meal fraction comprising *Brassica juncea* was prepared as described in Example 1 above. In addition, a blended meal fraction comprising 98 percent (w/w) of *Brassica juncea* and 2 percent (w/w) *Sinapis alba* was prepared by mixing *Brassica juncea* (98 percent (w/w)) and *Sinapis alba* seed (2 percent (w/w)) as described in Example 1. The pesticide efficacy against the seed- or soil-borne plant pathogen *Rhizoctonia solani* was examined as hereinafter described in this Example 3.

*Rhizoctonia solani* AG2 stock plate cultures were grown for 10 days on potato dextrose agar plus 0.05% streptomycin added to prevent bacterial growth. (Streptomycin has no effect on the growth or viability of *R. solani*). Ninety-six open mouthed, 500 mL Mason jars were covered with aluminium foil to keep them sterile after being removed from the autoclave and autoclaved for 20 minutes at 121° C., then cooled to room temperature. Ninety-six test plates (Petri dishes containing PDA+streptomycin) were made by cutting a fungal plug, approximately 0.5 cm diameter, from one of the stock plates and placing it the centre of the test plate.

Each mustard meal product was assayed at 8 concentrations per 50 mL water: 0 g (control), 0.025 g, 0.05 g, 0.075, 0.1 g, 0.25 g, 0.5 g, and 1.0 g, with 4 replicates; one jar per replicate. After the appropriate weight of each mustard meal product was added to the jars, 50 mL of sterile distilled water was poured into each jar and the jar was immediately covered with the inverted bottom half of a test plate containing a central plug of *R. solani*. The joint between the plate and the Mason jar was then wrapped and sealed with a double layer of laboratory parafilm to prevent contamination and drying out of the agar, as well as escape of mustard meal gases. The jars were incubated in the dark at room temperature (21° C.) and radial growth from the edge of the fungal plug was measured in mm at 1, 2, 3, and 5 days, by which time the *R. solani* mycelium had entirely covered the control plates (40 mm radius).

Data was analyzed statistically (ANOVA) using CoStat, Version 6.400, 2008, CoHort Software, Monterey Calif., USA, © 1998-2008 and means were compared in Tukey's HSD at P=0.05.

Three days after exposure to the mustard vapour in sealed jars, the inhibitory concentration (IC50) of *Brassica juncea*+*Sinapis alba* mustard meal was approximately 23 times less than that of *Brassica juncea* mustard meal alone and the IC90 was 14.8 times less (see: Table 1, FIG. 1). When the combined *Brassica juncea*+*Sinapis alba* meal was used, radial growth was significantly less at concentrations of 0.05 g per 50 mL and above (statistically different from *Brassica juncea* mustard meal alone in Tukey's HSD at P=0.05, Table 2).

Figure 2:
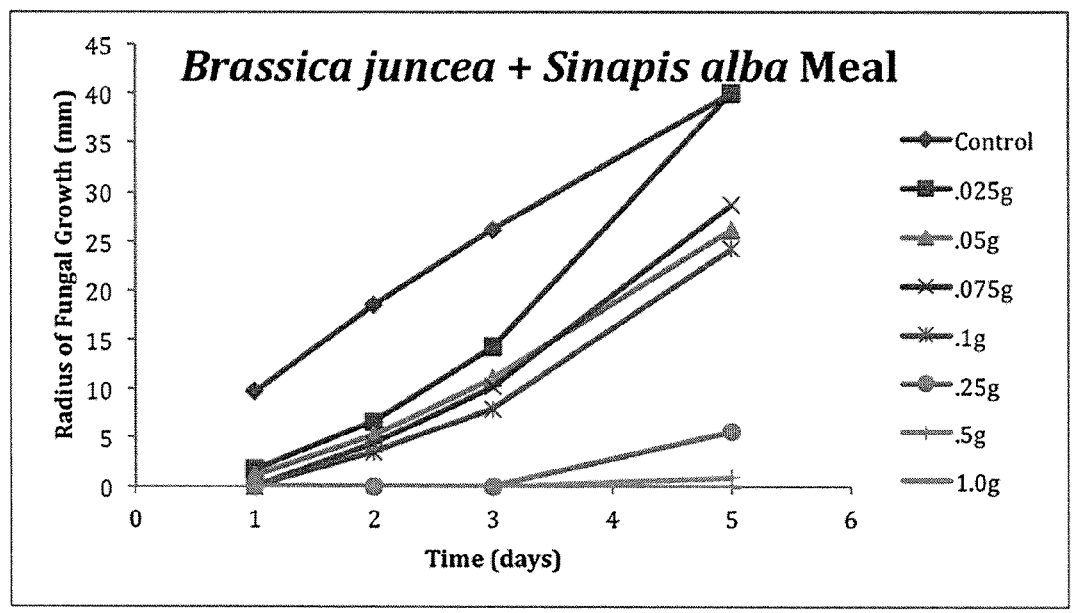
FIG. 2 depicts the radial growth of *R. solani* mycelium over time under exposure to different concentrations of a mixture of *Brassica juncea* and *Sinapis alba* mustard meal.
Figure 3:
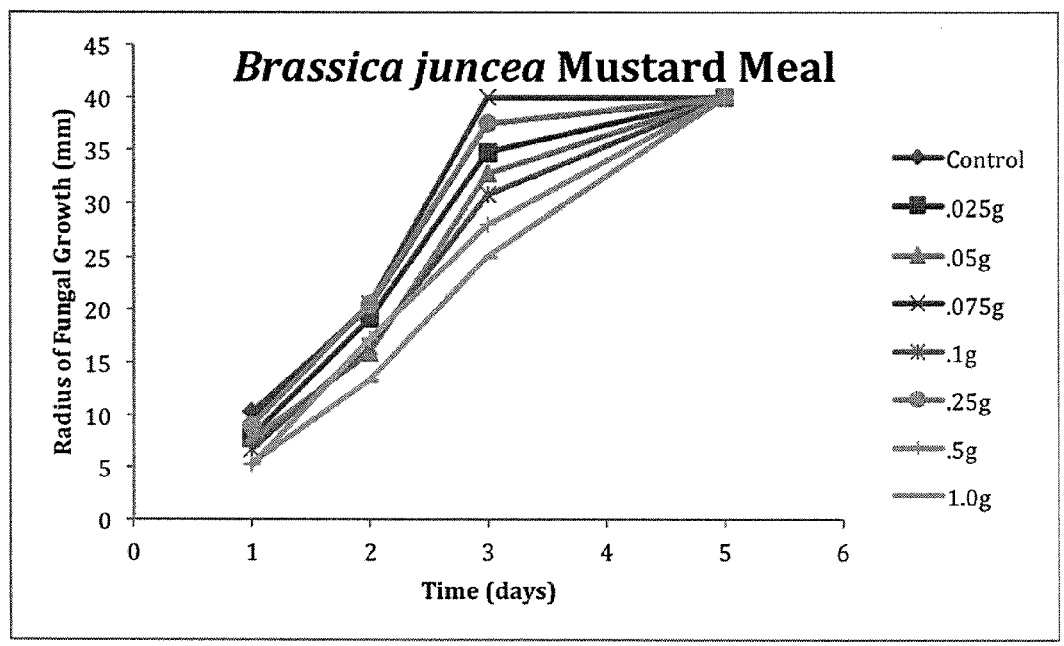
FIG. 3 depicts radial growth of *R. solani* mycelium over time under exposure to different concentrations of *Brassica juncea* mustard meal.

Colonies exposed to the *Brassica juncea* vapour alone had all reached the maximum radius of 40 mm by Day 5 (see: FIG. 3), while with the *Brassica juncea*+*Sinapis alba* only the control and the 0.025 g/50 mL concentration reached the maximum growth by Day 5 (see: FIG. 2). Thus, the IC50 and IC90 of each product was compared to the maximum of each control at Day 3 (see: Table 1).

The inhibitory effect of the *Brassica juncea*+*Sinapis alba* mustard meal on mycelial growth was not quite linear with concentration as the rate of growth increased between Days 3 and 5 across all concentrations except the control (see: FIGS. 1 and 2). The environmental conditions (temperature, light) were identical and consistent for the duration of the experiment.

TABLE 1

Concentration of each activated mustard meal product inhibiting mycelial growth of *Rhizoctonia solani* to 50 and 90% of the water control at three days after exposure.[1,2]

| Mustard Meal Product | Y = Mycelial Growth Rate Equation of Water Control | IW50 (g/50 ml) | IC50 (ppm) | IW90 (g/50 ml) | IC90 (ppm) |
|---|---|---|---|---|---|
| *Brassica juncea* Only | y = 30.814x + 3.5453 | 1.5076 | 30152 | 2.8057 | 56114 |
| 98% *Brassica juncea* + 2% *Sinapis alba* | y = 321.61x + 28.833 | 0.0658 | 1316 | 0.1902 | 3804 |

[1]Mean of 4 replicates per concentration per test product.

[2]IW = inhibitory weight of mustard meal pellets (g) per 50 mL water; IC = Inhibitory concentration (ppm).

TABLE 2

Mean radial growth of *R. solani* mycelium at five days after exposure to vapour from various concentrations of *Brassica juncea* mustard meal and 98% *Brassica juncea* + 2% *Sinapis alba*.[1,2]

| Day 5 [C] Mustard Meal (g/50 ml) | *Brassica juncea* + *Sinapis alba* | | *Brassica juncea* | |
|---|---|---|---|---|
| | Percent Inhibition (% relative to control) | Radial Growth (mm)[3] | Percent Inhibition (% relative to control) | Radial Growth (mm)[3] |
| 0 (Control) | 0 | 40 a | 0 | 40 a |
| 0.025 | 0 | 40 a | 0 | 40 a |
| 0.05 | 34.38 | 26.25 b | 0 | 40 a |
| 0.075 | 28.13 | 28.75 b | 0 | 40 a |
| 0.1 | 39.38 | 24.25 b | 0 | 40 a |
| 0.25 | 85.94 | 5.625 c | 0 | 40 a |
| 0.5 | 97.50 | 1 c | 0 | 40 a |
| 1 | 100 | 0 c | 0 | 40 a |

[1]Mean of four replicates per concentration per product, RCB design.
[2]Numbers in both columns followed by the same letter are not significantly different in Tukey's HSD at P = 0.05.
[3]Radius of 40 mm represents growth to the edge of the plate (i.e., the maximum growth on a media plate).

Example 4

Pesticide Efficacy of *Brassica juncea* and *Sinapis alba* Mustard Mixture Against *Pythium ultimum*

A mustard meal fraction comprising *Brassica juncea* was prepared as described in Example 1 above. In addition, a blended meal fraction comprising 98 percent (w/w) of *Brassica juncea* and 2 percent (w/w) *Sinapis alba* was prepared by mixing *Brassica juncea* (98 percent (w/w)) and *Sinapis alba* seed (2 percent (w/w)) as described in Example 1. The pesticide efficacy against the seed- or soil-borne plant pathogen *Pythium ultimum* Trow. var. *ultimum* was examined as hereinafter described in this Example 4.

*Pythium ultimum* var. *ultimum* stock plate cultures were grown for 4 days on V8 plus $CaCO_3$. Ninety-six open mouthed, 500 mL Mason jars were covered with aluminium foil to keep them sterile after being removed from the autoclave and autoclaved for 20 minutes at 121° C., then cooled to room temperature. Ninety-six test plates (Petri dishes containing V8+$CaCO_3$) were made by cutting a fungal plug, approximately 0.5 cm diameter, from one of the stock plates and placing it the centre of the test plate.

Each mustard meal product was assayed at 8 concentrations of per 50 mL water: 0 g (control), 0.025 g, 0.05 g, 0.075, 0.1 g, 0.25 g, 0.5 g, and 1.0 g, with 4 replicates; one jar per replicate. After the appropriate weight of each mustard meal product was added to the jars, 50 mL of sterile distilled water was poured into each jar and the jar was immediately covered with the inverted bottom half of a test plate containing a central plug of *P. ultimum*. The joint between the plate and the Mason jar was then wrapped and sealed with a double layer of laboratory parafilm to prevent contamination and drying out of the media, as well as escape of mustard meal gases. The jars were incubated in the dark at room temperature (21° C.) and radial growth from the edge of the fungal plug was measured in mm at 1, 2, 3, and 4 days, by which time the *P. ultimum* mycelium had entirely covered the control plates (40 mm radius).

Data was analyzed statistically (ANOVA) using CoStat, Version 6.400, 2008, CoHort Software, Monterey Calif., USA, © 1998-2008 and means were compared in Tukey-Kramer at P=0.05.

Figure 4:
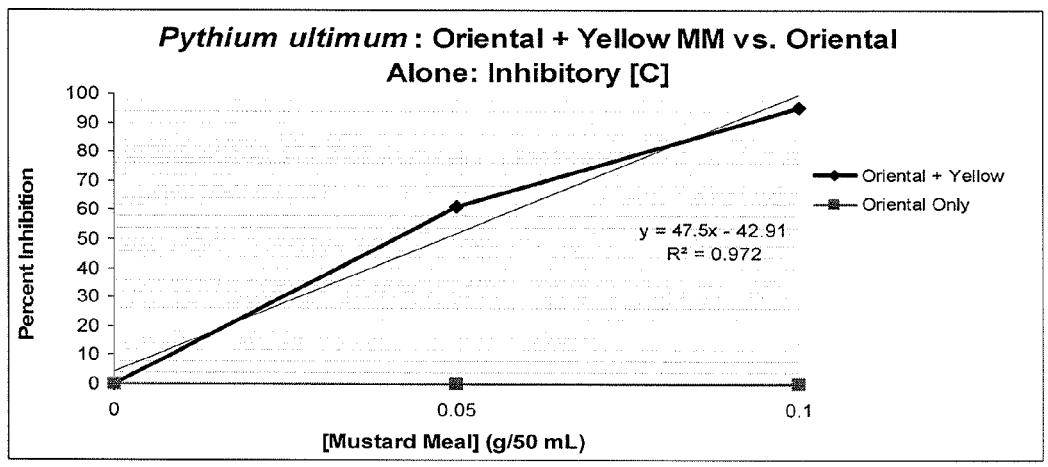
FIG. 4 depicts the inhibition of *P. ultimum* mycelial growth using various concentrations of a mixture of *Brassica juncea* and *Sinapis alba* mustard meal versus *Brassica juncea* meal alone.
Figure 5:
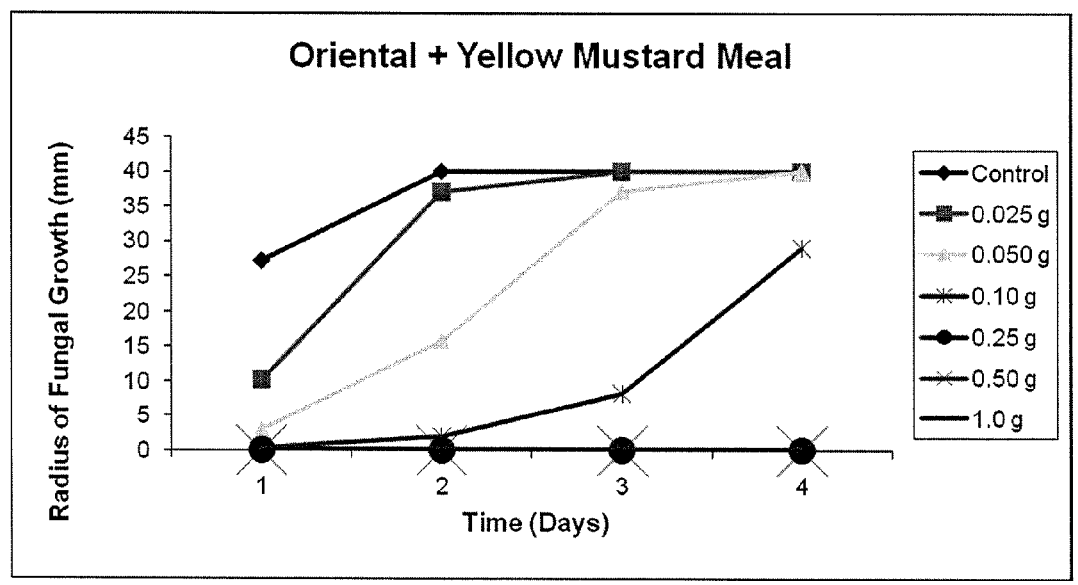
FIG. 5 depicts the radial growth of *P. ultimum* mycelium over time under exposure to different concentrations of a mixture of *Brassica juncea* and *Sinapis alba* mustard meal.
Figure 6:
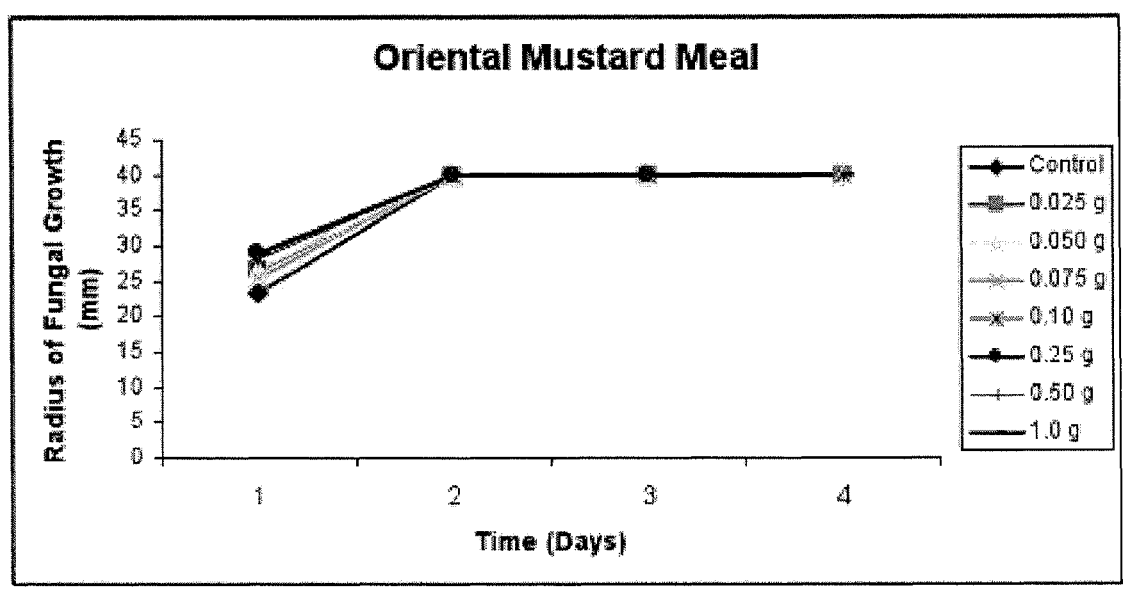
FIG. 6 depicts radial growth of *P. ultimum* mycelium over time under exposure to different concentrations of *Brassica juncea* mustard meal.

Results are presented in Tables 3 and 4 and FIGS. 4 to 6. All *Pythium* plugs exposed to the *Brassica juncea* mustard vapour alone reached the maximum growth radius of 40 mm by Day 2 (see: FIG. 4) while, with the *Brassica juncea*+ *Sinapis alba* only the control treatment (0.0 g/50 mL) reached the maximum growth by Day 2 (See FIG. 5). Thus, the IC50 and IC90 of each product were compared to the maximum growth of the control (0.0 g/50 mL) on Day 2 (Table 3). Growth was not inhibited at the highest concentration tested of *Brassica juncea* meal alone, 1.0 g/50 mL (20,000 ppm).

Two days after exposure to the mustard vapour in sealed jars, the 50% inhibitory concentration (IC50) of 98% *Brassica juncea*+2% *Sinapis alba* meal was 968 ppm and the IC90 was 1790 ppm, while the *Brassica juncea* meal alone did not inhibit growth at all at up to 20,000 ppm (see: Table 3, FIG. 4). When 98% *Brassica juncea*+2% *Sinapis alba* was used, the radial growth of *P. ultimum* was significantly less than with *Brassica juncea* alone at concentrations of 0.05 g per 50 mL and above (statistically different from *Brassica juncea* alone in Tukey-Kramer at P=0.05, Table 2).

TABLE 3

Concentration of each activated mustard meal product inhibiting mycelial growth of *Pythium ultimum* "in vitro" to 50 and 90% of the water control at two days after exposure.[1,2]

| Mustard Meal Product | Y = Mycelial Growth Rate Equation of Water Control | IW50 (g/50 mL) | IC50 (ppm) | IW90 (g/50 mL) | IC90 (ppm) |
|---|---|---|---|---|---|
| *Brassica juncea* Only[3] | Y = 0 | >1.0 | >20,000 | >1.0 | >20,000 |
| 98% *Brassica juncea* + 2% *Sinapis alba* | Y = 47.5x − 42.91 $R^2 = 0.972$ | 0.0484 | 968 | 0.0895 | 1790 |

[1]Mean of 4 replicates per concentration per test product.
[2]IW = inhibitory weight of mustard meal pellets (g) per 50 mL water; IC = inhibitory concentration (ppm).
[3]No inhibition of mycelial growth at any concentration up to 1.0 g/50 mL (20,000 ppm).

TABLE 4

Mean radial growth of *P. ultimum* mycelium at 2 days after exposure to vapour from various concentrations of 98% *Brassica juncea* + 2% *Sinapis alba* mustard meal and 100% *Brassica juncea* mustard meal.[1,2]

| Day 2 [C] Mustard Meal (g/50 mL) | 98% *Brassica juncea* + 2% *Sinapis alba* | | *Brassica juncea* only | |
|---|---|---|---|---|
| | Percent Inhibition (% relative to control) | Radial Growth (mm)[3] | Percent Inhibition (% relative to control) | Radial Growth (mm)[3] |
| 0 (Control) | 0 | 40.0 a | 0 | 40.0 a |
| 0.025 | 7.5 | 37.0 a | 0 | 40.0 a |
| 0.050 | 60.6 | 15.8 b | 0 | 40.0 a |
| 0.075[4] | — | — | 0 | 40.0 a |
| 0.10 | 95 | 2.0 c | 0 | 40.0 a |
| 0.25 | 100 | 0 c | 0 | 40.0 a |
| 0.50 | 100 | 0 c | 0 | 40.0 a |
| 1.0 | 100 | 0 c | 0 | 40.0 a |

[1]Mean of 4 replicates per concentration per product, RCB design.
[2]Numbers in both columns followed by the same letter are not significantly different in Tukey-Kramer at P = 0.05.
[3]Radius of 40 mm represents growth to the edge of the plate (i.e., the maximum growth on a media plate).
[4]Concentration 0.075 g deleted because all but one plug fell off the plate.

Example 6

Preparing a Mustard Meal Mixture of 90/10% (w/w) *Brassica juncea/Sinapis alba*

A mixture of *Brassica juncea/Sinapis alba* may be prepared by blending 900 kg grams dried *Brassica juncea* seed with 100 kg dried *Sinapis alba* seed using a standard hopper. Thereafter the methodology described in Example 1 may be used to prepare a blended mustard meal preparation comprising a mixture of 90/10% (w/w) *Brassica napus/Sinapis alba*. The AITC concentration in the blended mustard meal preparation may be determined and the blended mustard meal may be used as a pesticide, including as pesticide to control the pathogens *Rhizoctonia solani* and *Pythium ultimum*.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A composition for controlling fungicidal pests comprising a mixture of (a) a plant material obtained from a mustard plant of the species *Sinapis alba* comprising from about 0.3% to about 15% (w/w) of the mixture, and (b) a plant material obtained from a mustard plant of the species *Brassica juncea* comprising from about 99.7 to about 85% (w/w) of the mixture, and said composition comprising an effective amount of a glucosinolate breakdown product.

2. The composition according to claim 1 wherein the plant material obtained from a *Sinapis alba* mustard plant, or from *Brassica juncea* mustard plant is a processed plant material.

3. The composition according to claim 1 wherein the plant material obtained from a *Sinapis alba* mustard plant, or from *Brassica juncea* mustard plant is a mustard seed.

4. The composition according to claim 1 wherein the plant material obtained from a *Sinapis alba* mustard plant, or from *Brassica juncea* mustard plant is a seed meal.

5. The composition according to claim 1 further comprising a carrier.

6. The composition according to claim 1 wherein the glucosinolate breakdown product is an allyl thiocyanate, allyl isothiocyanate, allyl cyanide, 1-cyano-2-hydroxy-3-butene, goitrin or a hydroxyl benzol.

7. The composition according to claim 1 wherein the plant material obtained from *Sinapis alba* comprises about 2% (w/w) of said mixture and wherein the plant material obtained from *Brassica juncea* comprises about 98% (w/w) of said mixture.

8. The composition according to claim 1 wherein the glucosinolate breakdown product is allyl isothiocyanate and is present in the mixture at a concentration of at least 0.5% (w/w).

9. The composition according to claim 4 wherein the composition has a granular size selected from the group of granular sizes consisting of 0.01 mm to 0.25 mm; 0.25 mm to 0.75 mm; and 2 mm to 6 mm.

10. A method for preparing a fungicidal composition according to claim 1 comprising (a) mixing a plant material obtained from a mustard plant of the species *Sinapis alba*, with a plant material obtained from a mustard plant of the species *Brassica juncea*, said mixture comprising an effective amount of a glucosinolate breakdown product and (b) formulating said mixture into a fungicidal composition.

11. The method according to claim 10 wherein the plant material of the species *Sinapis alba* or the plant material of the species *Brassica juncea* is a mustard seed meal.

12. A method for controlling fungicidal pests comprising applying to a fungicidal pest a composition according to claim 1.

* * * * *